United States Patent
Ruppert et al.

(10) Patent No.: US 9,161,826 B2
(45) Date of Patent: Oct. 20, 2015

(54) PRODUCTION OF A NEGATIVE MOULD FOR USE IN PRODUCING OF A DENTAL PROSTHESIS, A TEMPORARY OR PERMANENT CROWN OR BRIDGE

(75) Inventors: Klaus Ruppert, Maintal (DE); Mario Beyer, Bad Homburg (DE)

(73) Assignee: HERAEUS KULZER GMBH, Hanau (DE)

(*) Notice: Subject to any disclaimer, the term of this patent is extended or adjusted under 35 U.S.C. 154(b) by 359 days.

(21) Appl. No.: 13/389,734

(22) PCT Filed: Aug. 9, 2010

(86) PCT No.: PCT/EP2010/004850
§ 371 (c)(1),
(2), (4) Date: Feb. 9, 2012

(87) PCT Pub. No.: WO2011/018196
PCT Pub. Date: Feb. 17, 2011

(65) Prior Publication Data
US 2012/0175800 A1 Jul. 12, 2012

(30) Foreign Application Priority Data

Aug. 12, 2009 (DE) .......................... 10 2009 036 980
Aug. 19, 2009 (DE) .......................... 10 2009 037 916

(51) Int. Cl.
*A61C 13/20* (2006.01)
*A61C 13/00* (2006.01)

(52) U.S. Cl.
CPC ............. *A61C 13/0004* (2013.01); *A61C 13/20* (2013.01); *A61C 13/0013* (2013.01)

(58) Field of Classification Search
CPC . A61C 13/0004; A61C 13/0013; A61C 13/20
USPC .............................................. 264/16, 19, 299
See application file for complete search history.

(56) References Cited

U.S. PATENT DOCUMENTS

| 5,690,490 A | 11/1997 | Cannon et al. |
| 6,152,731 A | 11/2000 | Jordan et al. |

(Continued)

FOREIGN PATENT DOCUMENTS

| DE | 40 05 570 A1 | 8/1991 |
| DE | 101 14 290 A1 | 10/2002 |

(Continued)

OTHER PUBLICATIONS

International Search Report issued by the European Patent Office Jan. 18, 2011.
German Search Report from corresponding application 10 2009 037 916.9.

*Primary Examiner* — James Sanders
(74) *Attorney, Agent, or Firm* — Norris McLaughlin & Marcus, P.A.

(57) ABSTRACT

For producing a mother matrix mould
  of a full or partial dental prosthesis or
  of a temporary crown or bridge
  or of a permanent crown or bridge,
  the data of a digitalised virtual model reflecting the status of the jaw is used to generate a data set
  of the digital tooth set-up of the full or partial dental prosthesis or
  of the temporary crown or bridge or
  of the permanent crown or bridge,
  based on which a rapid manufacturing or rapid prototyping method is used to produce a functional model of the full or partial dental prosthesis or of the temporary crown or bridge or of the permanent crown or bridge that is then invested in a curable elastic impression material from which the mother matrix mould is produced after curing the elastic impression material.

6 Claims, 1 Drawing Sheet

(56) References Cited

U.S. PATENT DOCUMENTS

| | | |
|---|---|---|
| 6,322,359 B1 | 11/2001 | Jordan et al. |
| 6,322,728 B1 | 11/2001 | Brodkin et al. |
| 6,881,360 B2 | 4/2005 | Stange et al. |
| 2004/0204787 A1 | 10/2004 | Kopelman et al. |
| 2004/0219490 A1 | 11/2004 | Gartner et al. |
| 2004/0220691 A1 | 11/2004 | Hofmeister et al. |
| 2006/0210945 A1 | 9/2006 | Savic et al. |
| 2007/0287131 A1 | 12/2007 | Ruppert et al. |
| 2008/0318189 A1 | 12/2008 | Brodkin et al. |

FOREIGN PATENT DOCUMENTS

| | | |
|---|---|---|
| DE | 101 50 256 A1 | 7/2003 |
| DE | 103 04 757 B4 | 7/2005 |
| DE | 10 2005 009 210 A1 | 8/2006 |
| DE | 10 2006 026 776 A1 | 12/2007 |
| EP | 1 243 230 A2 | 9/2002 |
| EP | 1 704 831 A1 | 9/2006 |
| EP | 1 864 627 A2 | 12/2007 |
| WO | 2004 087000 A1 | 10/2004 |
| WO | 2004 098443 A1 | 11/2004 |
| WO | 2009 042378 A1 | 4/2009 |

PRODUCTION OF A NEGATIVE MOULD FOR USE IN PRODUCING OF A DENTAL PROSTHESIS, A TEMPORARY OR PERMANENT CROWN OR BRIDGE

This application is a 371 of International Patent Application No. PCT/EP2010/004850, filed Aug. 9, 2010, which claims foreign priority benefit under 35 U.S.C. §119 of the German Patent Application No 10 2009 037 916.9 filed Aug. 19, 2009, and German Patent Application No. 10 2009 036 980.5 filed Aug. 12, 2009, the entire contents of which international and German patent applications are incorporated herein by reference.

The invention relates to the production of a mother matrix mould for subsequent production of a dental prosthesis or temporary or permanent crowns and bridges.

BACKGROUND

The production of prosthetic restorations such as crowns, bridges, partial or full dentures follows known methods. These include, e.g., the conventional powder/liquid technology methods that have been known for long and are described in the literature (e.g. EP 1 243 230 A2, U.S. Pat. No. 6,881,360 B2 and Ullmann (Dental Materials, Ullmann's Encyclopedia of Industrial Chemistry, Copyright 2002 by Wiley-VCH Verlag)).

In general, three different main classes of materials for production of full dentures are known. These are polymethylmethacrylate (PMMA)-based two component materials [commercially available as Palapress, Paladur (Heraeus Kulzer, DE), SR 3/60® Quick (Ivoclar, LI), Degupress® (Degussa-Hüls, DE)]; PMMA-free hot-curing materials [commercially available e.g. as Paladon® 65 (Heraeus Kulzer, DE), SR 3/60®, SR Ivocap® (Ivoclar, LI), Lucitone® (Dentsply, US)] and injection molded masses for thermoplastic processing.

Thermoplastic materials are heated and injected into a hollow space, usually through an injection molding method. A known method called "Polyapress"® is distributed, amongst others, by Bredent, Senden (DE). There have been numerous attempts to use polymers such as PVC, polyurethane, polyamide or polycarbonate (Ullmann's, ibid 5.1.5. Other Denture Resins).

Moreover, there are methods that are based on light- or microwave-cured 1-component materials (e.g. Versyo.com® made by Heraeus Kulzer) (Ullmann's, ibid 5.1.3. Light-Cured Polymers, 5.1.4. Microwave-Cured Polymers).

The work steps required for preparation of the processing of the plastic materials are the same for all of these materials.

Moreover, techniques for the build-up of layers are known in dental engineering. These are used in combination with light-curing materials in most cases, for example for veneering metal crowns or production of a prosthesis. The advantages of said methods include the level of control over the procedure and the ability to vary the colors in order to attain aesthetically pleasing dental work.

The use of rapid prototyping methods in dental engineering has also been proposed. These involve working with layers that can be polymerized (DE 101 14 290 A1, DE 101 50 256 A1) or ink jet powder printing (U.S. Pat. No. 6,322,728 B1).

Essentially, the production of full dentures involves the following steps:
dentist taking an impression;
a) fabrication of a model reflecting the shape of the jaw;
b) setting-up the artificial teeth in wax and carving the gingiva;
c) trying-in and correcting, if applicable, done by the dentist or the dental laboratory;
d) investing the wax prosthesis in dental plaster, silicone or agar agar;
e) removing the wax by boiling it out with hot water;
f) filling the hollow space thus generated with a denture plastic material (e.g. PalaXpress®),
g) curing and finishing the dental prosthesis.

Attempts are being made to an increasing degree to simplify this complex procedure. Accordingly, Heraeus Kulzer presented the "Filou® 28" set-up aid (EP 1 704 831 A1) at the IDS 2005. This aid was the first to reduce the time needed for setting-up the artificial teeth in wax.

Further developments reflect a trend of increased digitalization in dental engineering. Accordingly, ceramic restorations are already being produced through CAD/CAM technologies. Digital technologies are becoming distributed more broadly and are being accepted to an increasing degree in dentistry, e.g. scanning technologies (Lava C.O.S. made by 3M Espe) or virtual applicators and virtual set-ups of teeth.

DE 101 14 290 B4 described rapid prototyping methods for dental technology. Rapid Prototyping (German: schneller Prototypenbau) is a method for rapid production of sample components based on design data. Accordingly, rapid prototyping methods are manufacturing methods aiming to implement existing CAD data directly and rapidly in work pieces, if possible without manual detours or moulds. The relevant data interface for this group of methods is the STL format. The methods that have become known by the name of Rapid Prototyping since the 1980s are usually primary forming methods that build-up the work piece in layers from shapeless or neutral-shape material utilizing physical and/or chemical effects. It is a disadvantage of such layering methods that they always generate restorations of anisotropic structure such that post-processing, e.g. through additional light curing or thermal treatment, is required in order to attain the requisite stability. Another disadvantage is that aesthetically-pleasing coloring is very difficult to achieve. And the quality of the surface produced appears just as disadvantageous owing to the layered structure. The materials posses marked, tangible roughness on the order of tenths of millimeters.

The object is to simplify the classical production process that is described above. In this context, the disadvantages described above are to be circumvented or prevented.

The object is met by producing a mother matrix mould
of a full or partial dental prosthesis or
of a temporary crown or bridge
or of a permanent crown or bridge,
whereby the data of a digitalized virtual model reflecting the status of the jaw is used to generate a data set
of the digital tooth set-up of the full or partial dental prosthesis or
of the temporary crown or bridge or
of the permanent crown or bridge on the basis of which a rapid manufacturing or rapid prototyping method is used to produce a functional model of the full or partial dental prosthesis or temporary crown or bridge or permanent crown or bridge;
being invested in investment material;
and a mother matrix mould being produced from the cured investment material.

The term, Rapid Manufacturing or (German) Schnelle Fertigung, refers to methods and production procedures for rapid and flexible production of components and series' through tool-less fabrication based directly on the CAD data. The materials that are used include glass, metal, ceramic materials, plastic materials and new materials (such as UV-curing sol-gel, see, e.g., Multi Jet Modeling) [ . . . ].

Since Rapid Manufacturing always focuses on producing the end-product directly, it is fundamentally different from Rapid Prototyping and Rapid Tooling (rapid toolmaking).

Producing a positive likeness of the dental prosthesis as place holder, e.g., according to the rapid prototyping method, said positive likeness of the dental prosthesis can be invested in an elastic impression mass (e.g. alginate, agar-agar or silicone) and can subsequently be removed from the mould. The two-part hollow mould thus generated can be fitted with stock teeth and—after closing the two halves of the mould—the hollow space thus produced can be filled by casting with denture material.

The advantages of the method are as follows:

Established dental materials such as pre-formed stock teeth and time-proven denture materials can be used.

There is no limitation with regard to the selection of materials in terms of their functional, aesthetic and toxicological properties.

The mother matrix mould or flask can be produced according to an inexpensive conventional casting procedure and does not have to be built-up in layers in a time-consuming and expensive manner.

The production method according to the invention comprises, e.g., the following steps for full dentures:
Either
P-A Production of a model reflecting the shape of the jaw based on the impression taken by the dentist
P-B Digitalization of the model
or
PA+PB Provision of model data from the digital X-ray image or intraoral scan;
P-C Automatic digital set-up using previously entered 3D models of artificial teeth, as described, e.g., in DE 103 04 757 B4;
P-D Digital production of a functional model of the prosthesis from the data of the model from step C according to the rapid prototyping/rapid manufacturing method, optionally including the provision of casting channels;
P-E Investing the functional model, preferably in silicone;
P-F Cutting-open the investment and removing the functional prosthesis from the mould;
P-G Inserting the stock teeth;
P-H Filling the remaining hollow space with denture plastic material (e.g. PalaXpress®);
P-I Finishing the prosthesis.

The functional model can be produced through rapid manufacturing or rapid prototyping methods such as milling methods, 3D printing methods, stereolithography, laser sintering or other rapid prototyping methods. As an option, the surface of the functional model can be post-processed after production, in particular through smoothing and/or polishing. The functional model can consist either of a stable polymer or a wax-like material which is still amenable to slight geometric corrections while trying it in in the mouth of the patient as an option.

The functional model is preferably invested using a commercially available model-making silicone, possibly also using reinforcing elements, such as, e.g., mesh structures which provide additional mechanical stability to the investment and thus improve the geometric accuracy of fit. The silicone is selected such that it has sufficiently high viscosity in its cured state for the mould to be stable and the stock teeth to be held in the intended positions during the subsequent steps of processing. However, the silicone must not be too solid either to allow the finished prosthesis to be removed from the mould without difficulty.

Figure 1A:
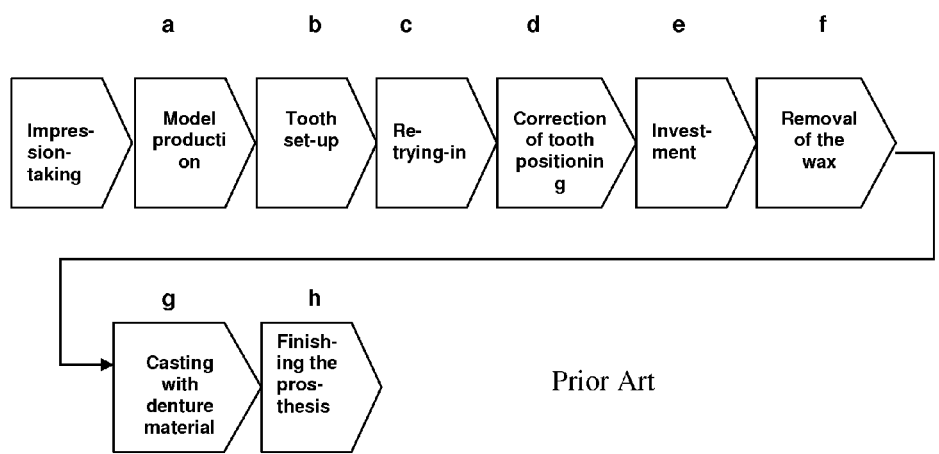
FIG. 1A shows a flow diagram of the standard procedure according to the prior art for the production of full dentures.
Figure 1B:
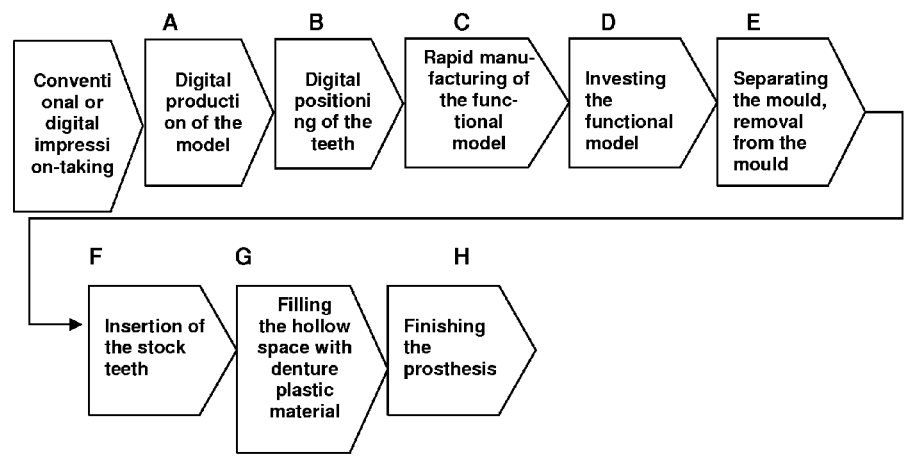
FIG. 1B shows a flow diagram of the method according to the invention for the production of full dentures.

The invention is illustrated in more detail based on the flow diagrams shown in FIGS. 1A and 1B: The initial deviations from the traditional process are the production and handling of a digital model and virtual handling of the model during tooth set-up. Methods of this type and corresponding devices are described, e.g., in U.S. Pat. No. 6,152,731 A, U.S. Pat. No. 6,322,359 B1 and DE 103 04 757 B4. The essential feature of the invention is the production of a functional model through a rapid manufacturing or rapid prototyping method.

The functional model is then invested and the hollow space for casting the dental prosthesis is generated once the functional model is removed from the mould. Since the teeth have already been set-up virtually, the denture teeth can be placed directly in the sites provided for this purpose. The further processing (casting with denture base material and curing) is identical to the traditional method.

The method according to the invention is advantageous in that, while traditional materials are used for processing, the advantages of virtual articulation and tooth set-up can be utilized.

Another trying-in in the patient, which is obligatory in the traditional method, is not mandatory in this method. Dispensing with a trying-in session of this type also dispenses with having to send shipments back and forth between dental office and dental laboratory.

The functional model according to the invention can also be applied to the production of crowns and bridges described, e.g., in EP 1 864 627 A2.

Therefore, the invention also relates to a method for the production of crowns and bridges according to a digitalized virtual model that reflects the jaw status, comprising the steps
tKB-A taking a digital impression of the jaw and tooth status before the preparation;
tKB-B taking a digital impression of the jaw and tooth status after the preparation;
tKB-C digital production of the temporary crown or bridge
tKB-D producing a functional model from the digital data using a rapid manufacturing or rapid prototyping method;
tKB-E investing the functional model in an elastic impression material (e.g. silicone, agar-agar, alginate, dental plaster, refractory investment material);
tKB-F separating the investment and removing the functional model;
tKB-G filling a crown & bridge material into the remaining hollow space;
tKB-H solidification of the crown & bridge material.

The functional model can also be used in the production of ceramic crowns or bridges, which is also described, e.g., in EP 1 864 627 A2.

It is then a method for the production of permanent crowns and bridges made of ceramic materials according to a digitalized virtual model that reflects the jaw status, comprising the steps
dKB-A providing a data set from the digital impression of the jaw and tooth status before the preparation;
dKB-B providing a data set from the digital impression of the jaw and tooth status after the preparation;

dKB-C digital production of the crown or bridge dKB-D producing a functional model from the digital data dKB-E investing the functional model, preferably in an elastic impression material made of a porous, absorbent material, such as, e.g., dental plaster, taking the sinter shrinkage into consideration tKB-F separating the investment and removing the functional model;

dKB-G congruent closing of the investment dKB-H producing the mother matrix mould (rapid manufacturing or rapid prototyping)

tKB-G filling a ceramic slurry into the remaining hollow space dKB-J removal from the mould once stability of shape is attained dKB-K optional further drying dKB-L optional sintering of the ceramic blank, and dKB-M firing.

The invention claimed is:

1. Method for the production of full or partial dentures according to a digitalised virtual model reflecting the jaw status, comprising the steps
   - P-A generating a data set of the virtual model from data of the digital record of the jaw status and jaw relation or from the impression taken by the dentist;
   - P-B digital tooth set-up based on the data set from step P-A;
   - P-C generating a functional model from the data set of the digital tooth set-up PB using a rapid manufacturing or rapid prototyping method;
   - P-D investing the functional model from step PC in a curable elastic impression material and curing the curable elastic impression material;
   - P-E removing the functional model from the cured elastic impression material while the investment stays behind;
   - P-F inserting stock teeth into the investment;
   - P-G filling the remaining hollow space of the investment with denture plastic material to form the dentures;
   - P-H curing and finishing the dentures.

2. Method according to claim 1, whereby step PB is automated.

3. Method according to claim 1, whereby the curable elastic impression material is silicone, agar-agar, alginate or a transparent light-curing plastic material.

4. Method according to claim 1, whereby the remaining hollow space is filled with denture plastic material according to an injection method.

5. Method according to claim 1, whereby the remaining hollow space is filled with denture plastic material according to the plugging-pressing method.

6. Method according to claim 1, whereby the remaining hollow space is filled with denture plastic material according to the casting method.

* * * * *